US00PP16577P2

(12) United States Plant Patent
Olesen

(10) Patent No.: US PP16,577 P2
(45) Date of Patent: May 30, 2006

(54) MINIATURE ROSE PLANT NAMED 'POULPAH026'

(50) Latin Name: ***Rosa* hybrid**
Varietal Denomination: Poulpah026

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 129 days.

(21) Appl. No.: 11/001,949

(22) Filed: Dec. 1, 2004

(51) Int. Cl.
*A01H 5/00* (2006.01)

(52) U.S. Cl. ..... Plt./116

(58) Field of Classification Search ..... Plt./116, Plt./118, 119
See application file for complete search history.

*Primary Examiner*—Anne Marie Grunberg
*Assistant Examiner*—June Hwu

(57) ABSTRACT

A new rose plant that has abundant, pink orange blended flowers and attractive foliage. The variety successfully propagates from softwood cuttings and is suitable for year-round production in commerical glasshouses. This new and distintct variety has shown to be uniform and stable in the resulting generations from asexual propagation.

1 Drawing Sheet

Botanical classification: *Rosa* hybrid.
Variety denomination: 'Poulpah026'.

SUMMARY OF THE INVENTION

The present invention constitutes a new and distinct variety of rose plant which originated from a controlled crossing between the female parent, an unnamed seedling, and the male pollen parent, an unpatented rose named 'Kormutric'. The two parents were crossed and the resulting seeds were planted in a controlled environment. The new variety is named 'Poulpah026'.

The new rose may be distinguished from its seed parent, by the following combination of characteristics:

1. Flower buds of the seed parent are shorter in length than those of 'Poulpah026'.
2. The seed parent has 35 to 45 petals, while 'Poulpah026' has 50 to 55 petals.

The new variety may be distinguished from its pollen parent in that 'Kormutric' has a general tonality of flower color which is yellow to yellow orange, while 'Poulpah026' is Red Group 35D with intonations of Orange Group 29B.

The objective of the hybridization of this rose variety for commercial culture was to create a new and distinct variety with unique qualitites, such as:

1. Uniforms and abundant Pink and orange blend flowers;
2. Vigorous and compact growth;
3. Year-round flowering under glasshouse conditions;
4. Suitability for production from softwood cuttings in pots;
5. Durable flowers and foliage which make a variety suitable for distruibution in the floral industry.

This combination of qualities is not present in previously available commercial cultivars of this type, known to the inventor, and distinguish 'Poulpah026' from all other varieties of which we are aware.

As part of the rose development program, Mogens N. Olesen germinated the seeds from the aforementioned hybridization and conducted elevaluations on the resulting seedlings in a controlled environment in Fredensborg, Denmark.

'Poulpah026' was selected by the inventor as a single plant from the progeny of the hybridization in June 2001.

Asexual reproduction of 'Poulpah026' by cuttings and traditional budding was first done by Mogens N. Olesen in the nursery in Fredensborg, Denmark in April 2002. This initial and other subsequent propagations conducted in controlled environments have demonstrated that the characteristics of 'Poulpah026' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah026'. Specifically illustrated in the drawing:

FIG. 1.1; Flower buds at various stages of development;

FIG. 1.2; Open flower, above view;

FIG. 1.3; Sepals, receptacle, and pedicel;

FIG. 1.4; Bare stem;

FIG. 1.5; Petals, detached;

FIG. 1.6; Juvenile leaves showing anthocyanin;

FIG. 1.7; Mature leaves.

DETAILED DESCRIPTION OF THE VARIETY

The following is a description of 'Poulpah026', as observed in its growth in glasshouses in Odense, Denmark. Observed plants were cultivated for a period of 16 weeks in 15 cm pots. Color references are made using The Royal Horticultural Society (London, England) Colour Chart, 2001, except where common terms of color are used.

For a comparison, several physical characteristics of 'Poulnil', a rose variety from the same inventor described and illustrated in U.S. Plant Pat. No. 13,301 issued Dec. 3, 2002, are compared to 'Poulpah026' in Chart 1.

CHART 1

| | 'Poulpah026' | 'Poulnil' |
|---|---|---|
| Petalage. | Very double; 50 to 55 petals. | Semi-double; 16 to 19 petals. |
| Bud color as sepals unfold. | Orange Group 29B with splotches of Red Group 48B. | Orange-Red Group 31A to 31B. |
| General tonality of flower | Red Group 38D with intonations of Orange Group 29B. | On open flower Red-Purple Group 65 C/D with intonations of Yellow Group 3B. |

FLOWER AND FLOWER BUD

Blooming habit: Continuous.

Flower bud:

*Size.*—Upon opening, 33 mm in length from base of receptacle to end of bud. 15 mm in diameter.

*Bud form.*—Ovoid to oblong.

*Bud color.*—As sepals unfold, petals are Orange Group 29B with splotches of Red Group 48B. Other observed intonations are Greyed-Red Group 179C.

*Sepals.*—Upper Surface: Color: Yellow-Green Group 147A at the apex. Green Group 137B at the base. Surface: Weak to medium pubescence observed. Lower Surface: Color: Yellow-Green Group 144B to Yellow-Green Group 147A. Other intonations: Anthocyanic intonations of Greyed-Purple Group 183A at sepal apecies. Occasionally, sepals exhibit splotches of Red Group 45B. Texture: Smooth with few stipitate glands. Shape: Apex: Cirrhose. Occasionally, sepals broaden somewhat at the apex. Base: Flat at union with receptacle. Margins: Margins have strong foliaceous appendages on three of the five sepals. Size: 40 mm (l) by 5 mm (w).

*Receptacle.*—Surface Texture: Smooth. Shape: Funnel shaped. Size: 8 mm (h)×10 mm (w). Color: Yellow-Green Group 144A.

*Pedicel.*—Surface: Smooth. Length: 30 to 40 mm. Diameter: 4 mm. Color: Yellow-Green Group 144A. Strength: Strong.

*Borne.*—Singularly.

Flower bloom:

*Fragrance.*—Moderate floral scent.

*Duration.*—As a pot plant, flowers last up to 28 days. Petals remain attached to the receptacle after flowers have matured.

*Size.*—Normally 65 to 70 mm in diameter when open. Depth is 30 mm on average.

*Form.*—High centered, very double, with a high pointed center which is tightly closed.

*Side view shape, upon opening.*—Upper part: Flat. Lower part: Flat.

*Side view shape, after opening.*—Upper part: Flattened convex. Lower part: Concave.

*Petalage.*—50 to 55 petals under normal conditions, 10 of which are petaloids.

Flower color:

*Upon opening, petals.*—Outermost petals: Upper Surface: Orange Group 27B with intonations of Yellow Group 13D. Lower Surface: Orange Group 27C with an overlay of Red Group 38A. Red Group 54B at basal zone. Innermost petals: Upper Surface: Orange Group 27B with intonations of Yellow Group 13D. Lower Surface: Orange Group 27C with an overlay of Red Group 38A. Red Group 54B at basal zone.

*Upon opening, basal petal spots.*—Upper Surface: Yellow Group 6A. Lower Surface: Yellow Group 4B.

*After opening, petals.*—Outermost guard petals: Upper Surface: Green Group 145B to 145C with intonations of Red Group 49A at the basal zone. Lower Surface: Green Group 145B with intonations of Red Group 48A to Red-Purple Group 58C at the basal zone. Innermost petals: Upper Surface: Orange Group 27C. Yellow Group 13D blended in at the middle and basal zone. Lower Surface: Yellow-Orange Group 19C with an overlay of Red Group 38A.

*After opening, basal petal spots.*—Outermost petals: Upper Surface: Yellow Group 4A. Lower Surface: Yellow Group 4B.

General tonality: On open flower Red Group 38D with intonations of Orange Group 29B. No change in general tonality at the end of the $14^{th}$ day.

Petals:

*Petal reflex.*—Outer petals are somewhat reflexed.

*Petal margin.*—Entire. Weak undulations of margin observed. Some petals have a cleft at the apex of the margin.

*Shape.*—Rounded to broad elliptical. Base: Acute. Apex: Rounded to occasinally cuspidate.

*Size.*—Petal length is 33 to 43 mm (l)×25 to 46 mm (w).

*Texture.*—Smooth.

*Thickness.*—Above average.

Petaloids:

*Quantity.*—Normally 10.

*Size.*—18 mm (l)×15 mm (w).

*Shape.*—Irregular and asymmetric.

*Color.*—Upper Surface: Orange Group 27B with intonations of Yellow Group 13D. Lower Surface: Orange Group 27C with an overlay of Red Group 38A. Red Group 54B at basal zone.

Reproductive organs:

*Pollen.*—None observed.

*Anthers.*—Color: Yellow Group 4D. Margins are Yellow Group 9A. Quantity: 65 to 75.

*Filaments.*—Color: Yellow Group 9A. Length: 4 to 5 mm.

*Pistils.*—Length: 5 mm. Quantity: 60 to 70.

*Stigmas.*—Slightly superior in location relative to the length of the filaments and the height of the anthers. Color: Yellow Group 4B.

*Styles.*—Color: Yellow-Green Group 150D with Red-Purple Group 61B.

*Seed formation.*—None observed.

PLANT

Plant growth: Moderate, upright to bushy. When grown as a 15 cm pot plant on its own roots, the average height of the plant itself is 20 cm and the average width is 20 cm.

Stem:

*Color.*—Young wood: Yellow-Green Group 144A. Older wood: Yellow-Green Group 146A.

*Diameter.*—3.5 to 4 mm.

*Internodal distance.*—25 mm.

*Length of stems.*—On average canes are 17 cm from the base of the stem to the flowering portion.

*Surface texture.*—Young wood: Smooth. Older wood: Rough with small prickles.

Thorns:

*Incidence.*—2 to 3 per 10 cm of stem.

*Color.*—Juvenile thorns are Greyed-Red Group 180C to Greyed-Purple Group 183A. Mature thorns are Greyed-Red Group 180C to Greyed-Yellow Group 162A.

*Shape.*—Upper side: Flat. Lower side: Concave.

Plant foliage: Normal number of leaflets on normal leaves in middle of the stem: 5 leaflets.

*Compound left size.*—90 mm (l)×65 mm (w).

*Quantity.*—3 leaves per 10 cm of stem.

*Color juvenile foliage:*

*Upper leaf surface.*—Yellow-Green Group 144A with anthocyanin at the margins Greyed-Red Group 178A.

*Lower leaf surface.*—Yellow-Green Group 146B with anthocyanin at the margins Greyed-Red Group 173A.

*Color of intermediate foliage:*

*Upper leaf surface.*—Yellow-Green Group 147A with anthocyanic intonations of Greyed-Purple Group 183A to 187A.

*Lower leaf surface.*—Yellow-Green Group 147A with intonations of Greyed-Purple Group 183A to 187A.

*Color of mature foliage:*

*Upper leaf surface.*—Yellow-Green Group 147A.

*Lower leaf surface.*—Yellow-Green Group 147A.

Plant leaves and leaflets:

*Stipules.*—Size: 8 mm. Shape: Linear, slightly broad based with outward extending apecies. Margins: Finely serrated with few stipitate glands. Color: Yellow-Green Group 147A.

*Petiole.*—Length: 20 mm. Diameter: 1.25 mm. Color: Upper surface is Yellow-Green Group 146A with intonations of Greyed-Purple Group 183A. Lower surface is Yellow-Green Group 146C. Underneath: Few stipitate glands observed.

*Rachis.*—Size: 30 mm. Color: Yellow-Green Group 146A with intonations of Greyed-Purple Group 183A. Underneath: Numerous rough stipitate glands observed.

*Leaflet.*—Size: 50 mm (l)×30 mm (w). Edge: Serrated. General Shape: Ovate. Apex Shape: Acuminate. Base Shape: Obtuse. Texture: Smooth. Thickness: Average to thin. Arrangement: Odd pinnate. Venation: Reticulate. Leaf Gloss: Matte finish.

Disease resistance: Average resistance to mildew, black spot, and *Botrytis* under normal growing conditions in Fredensborg, Denmark.

It is claimed:

1. A new and distinct variety of rose plant of the miniature class named 'Poulpah026', illustrated and described herein, due to its abundant, pink and orange blend flowers, vigorous growth, compact habit, suitability for production from softwood cuttings in pots, and durable flowers and foliage that make the variety suitable for distribution in the floral industry.

* * * * *

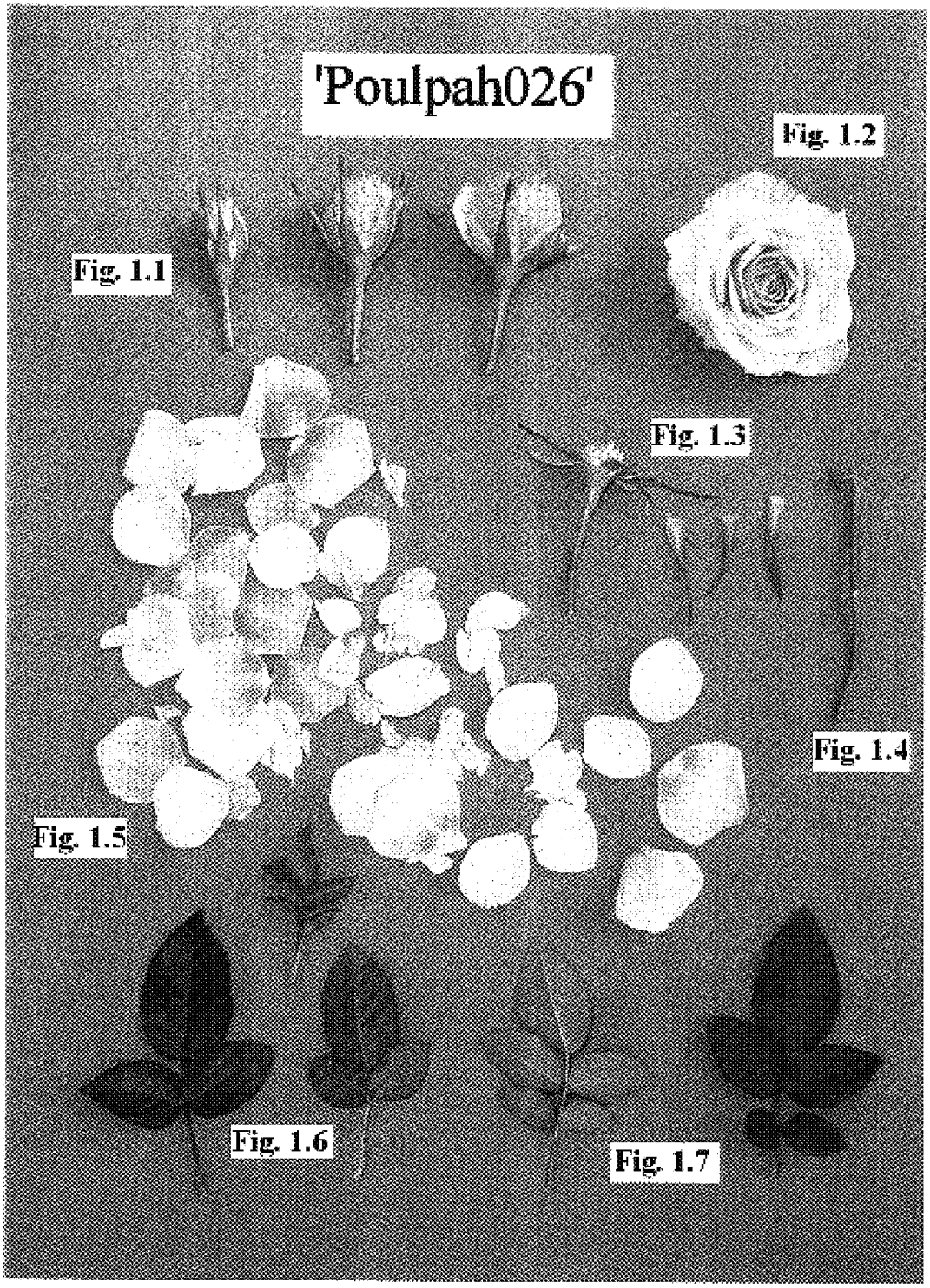
'Poulpah026'
Fig. 1.1
Fig. 1.2
Fig. 1.3
Fig. 1.4
Fig. 1.5
Fig. 1.6
Fig. 1.7